United States Patent
Kopel et al.

(10) Patent No.: US 12,310,677 B2
(45) Date of Patent: *May 27, 2025

(54) DEFORMABLE REGISTRATION OF COMPUTER-GENERATED AIRWAY MODELS TO AIRWAY TREES

(71) Applicant: Covidien LP, Mansfield, MA (US)

(72) Inventors: Evgeni Kopel, Barkan (IL); Oren P. Weingarten, Hod-Hasharon (IL); Alexander Nepomniashchy, Herzliya (IL); Nicolas J. Merlet, Jerusalem (IL)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/416,971

(22) Filed: Jan. 19, 2024

(65) Prior Publication Data
US 2024/0156541 A1 May 16, 2024

Related U.S. Application Data

(63) Continuation of application No. 16/696,705, filed on Nov. 26, 2019, now Pat. No. 11,877,806.
(Continued)

(51) Int. Cl.
*A61B 5/05* (2021.01)
*A61B 1/267* (2006.01)
(Continued)

(52) U.S. Cl.
CPC ............ *A61B 34/20* (2016.02); *A61B 1/2676* (2013.01); *A61B 10/04* (2013.01);
(Continued)

(58) Field of Classification Search
CPC ....... A61B 34/20; A61B 1/2676; A61B 10/04; A61B 18/1815; A61B 34/10; A61B 5/055; A61B 6/032; A61B 2018/00541; A61B 2018/00577; A61B 2034/105; A61B 2034/2051; A61B 2034/2065; A61B 6/5247; A61B 5/062; A61B 5/08; A61B 5/6852; A61B 6/50; A61B 18/1492; A61B 2017/00809; A61B 2018/0212; A61B 2034/107; A61B 2034/2048;
(Continued)

(56) References Cited

U.S. PATENT DOCUMENTS 1,049,999 A 1/1913 Connor
1,058,870 A 4/1913 Kinder
(Continued)

FOREIGN PATENT DOCUMENTS

BR 0013237 A 7/2003
BR 0116004 A 6/2004
(Continued)

*Primary Examiner* — Joel Lamprecht
(74) *Attorney, Agent, or Firm* — Weber Rosselli & Cannon LLP (57) ABSTRACT

A system for registering a luminal network to a 3D model of the luminal network includes a computing device configured to identify potential matches in the 3D model with location data of a location sensor, assigning one of the potential matches a registration score based on a deformation model applied to the 3D model, and displaying the potential match having the highest registration score.

20 Claims, 7 Drawing Sheets

Related U.S. Application Data (60) Provisional application No. 62/776,152, filed on Dec. 6, 2018.

(51) Int. Cl.
*A61B 10/04* (2006.01)
*A61B 18/18* (2006.01)
*A61B 34/10* (2016.01)
*A61B 34/20* (2016.01)
*G16H 50/50* (2018.01)
*A61B 5/055* (2006.01)
*A61B 6/03* (2006.01)
*A61B 18/00* (2006.01)

(52) U.S. Cl.
CPC .......... *A61B 18/1815* (2013.01); *A61B 34/10* (2016.02); *G16H 50/50* (2018.01); *A61B 5/055* (2013.01); *A61B 6/032* (2013.01); *A61B 2018/00541* (2013.01); *A61B 2018/00577* (2013.01); *A61B 2034/105* (2016.02); *A61B 2034/2051* (2016.02); *A61B 2034/2065* (2016.02)

(58) Field of Classification Search
CPC ...... A61B 2034/2061; A61B 2090/376; A61B 2018/1861; A61B 2034/2072; A61B 2090/374; A61B 2090/3762; A61B 2034/101; G16H 50/50; G06T 7/33; G06T 2207/30061
See application file for complete search history.

(56) References Cited

U.S. PATENT DOCUMENTS

| | | |
|---|---|---|
| 5,057,494 A | 10/1991 | Sheffield |
| 5,321,113 A | 6/1994 | Cooper et al. |
| 6,003,517 A | 12/1999 | Sheffield et al. |
| 6,226,548 B1 | 5/2001 | Foley et al. |
| 6,235,038 B1 | 5/2001 | Hunter et al. |
| 6,402,762 B2 | 6/2002 | Hunter et al. |
| 6,851,855 B2 | 2/2005 | Mitschke et al. |
| 6,925,339 B2 | 8/2005 | Grimm et al. |
| 6,932,823 B2 | 8/2005 | Grimm et al. |
| 6,988,009 B2 | 1/2006 | Grimm et al. |
| 7,097,357 B2 | 8/2006 | Johnson et al. |
| 7,341,063 B2 | 3/2008 | Garbibaldi et al. |
| 7,366,562 B2 | 4/2008 | Dukesherer et al. |
| 7,556,428 B2 | 7/2009 | Sukovic et al. |
| 7,599,730 B2 | 10/2009 | Hunter et al. |
| 7,697,972 B2 | 4/2010 | Verard et al. |
| 7,818,044 B2 | 10/2010 | Dukesherer et al. |
| 7,885,441 B2 | 2/2011 | Node-Langlois et al. |
| 7,971,341 B2 | 7/2011 | Dukesherer et al. |
| 7,981,038 B2 | 7/2011 | Kanade et al. |
| 7,995,827 B2 | 8/2011 | Wagner et al. |
| 8,010,177 B2 | 8/2011 | Csavoy et al. |
| 8,046,052 B2 | 10/2011 | Verard et al. |
| 8,060,185 B2 | 11/2011 | Hunter et al. |
| 8,175,681 B2 | 5/2012 | Hartmann et al. |
| 8,175,804 B2 | 5/2012 | Andoh |
| 8,218,847 B2 | 7/2012 | Averbuch et al. |
| 8,233,963 B2 | 7/2012 | Hartmann et al. |
| 8,239,001 B2 | 8/2012 | Verard et al. |
| 8,248,413 B2 | 8/2012 | Gattani et al. |
| 8,271,069 B2 | 9/2012 | Jascob et al. |
| 8,290,572 B2 | 10/2012 | Martinelli et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,335,359 B2 | 12/2012 | Fidrich et al. |
| 8,364,245 B2 | 1/2013 | Kruecker |
| 8,452,068 B2 | 5/2013 | Averbuch et al. |
| 8,467,852 B2 | 6/2013 | Csavoy et al. |
| 8,475,470 B2 | 7/2013 | Jako |
| 8,480,588 B2 | 7/2013 | Kanade et al. |
| 8,483,434 B2 | 7/2013 | Buehner et al. |
| 8,494,613 B2 | 7/2013 | Markowitz et al. |
| 8,543,189 B2 | 9/2013 | Paitel et al. |
| 8,611,983 B2 | 12/2013 | Glossop |
| 8,644,907 B2 | 2/2014 | Hartmann et al. |
| 8,694,075 B2 | 4/2014 | Groszmann et al. |
| 8,706,184 B2 | 4/2014 | Mohr et al. |
| 8,712,503 B2 | 4/2014 | Henning |
| 8,731,641 B2 | 5/2014 | Hartmann et al. |
| 8,737,708 B2 | 5/2014 | Hartmann et al. |
| 8,827,934 B2 | 9/2014 | Chopra et al. |
| 8,900,131 B2 | 12/2014 | Chopra et al. |
| 9,002,437 B2 | 4/2015 | Yaroshenko et al. |
| 9,095,252 B2 | 8/2015 | Popovic |
| 9,129,359 B2 | 9/2015 | Averbuch et al. |
| 9,241,657 B2 | 1/2016 | Vollmer et al. |
| 9,271,803 B2 | 3/2016 | Averbuch et al. |
| 9,289,270 B2 | 3/2016 | Gielen et al. |
| 9,375,268 B2 | 6/2016 | Long |
| 9,480,415 B2 | 11/2016 | Wald et al. |
| 9,547,910 B2 | 1/2017 | Hamza et al. |
| 9,554,812 B2 | 1/2017 | Inkpen et al. |
| 9,566,043 B2 | 2/2017 | Kanade et al. |
| 9,640,070 B2 | 5/2017 | Griswold et al. |
| 9,649,160 B2 | 5/2017 | Walt et al. |
| 9,675,424 B2 | 6/2017 | Jascob et al. |
| 9,717,442 B2 | 8/2017 | Jacobsen et al. |
| 9,801,566 B2 | 10/2017 | Verard et al. |
| 9,854,991 B2 | 1/2018 | Bzostek et al. |
| 9,861,338 B2 | 1/2018 | Kanade et al. |
| 9,867,674 B2 | 1/2018 | Hartmann et al. |
| 9,918,659 B2 | 3/2018 | Chopra et al. |
| 9,918,797 B2 | 3/2018 | Birkenbach et al. |
| 10,004,558 B2 | 6/2018 | Long et al. |
| 10,010,373 B2 | 7/2018 | Canfield et al. |
| 10,070,802 B2 | 9/2018 | Paitel et al. |
| 10,111,717 B2 | 10/2018 | Lui et al. |
| 10,166,078 B2 | 1/2019 | Sela et al. |
| 10,194,897 B2 | 2/2019 | Cedro et al. |
| 10,264,947 B2 | 4/2019 | Holsing et al. |
| 10,274,958 B2 | 4/2019 | DelMarco et al. |
| 10,285,623 B2 | 5/2019 | Averbuch et al. |
| 10,346,976 B2 | 7/2019 | Averbuch et al. |
| 10,373,719 B2 | 8/2019 | Soper et al. |
| 10,376,178 B2 | 8/2019 | Chopra |
| 10,390,892 B2 | 8/2019 | Witcomb et al. |
| 10,405,753 B2 | 9/2019 | Sorger |
| 10,418,705 B2 | 9/2019 | Morgan et al. |
| 10,426,554 B2 | 10/2019 | Siewerdsen et al. |
| 10,446,931 B2 | 10/2019 | Morgan et al. |
| 10,449,005 B2 | 10/2019 | Christian et al. |
| 10,478,092 B2 | 11/2019 | Averbuch et al. |
| 10,478,162 B2 | 11/2019 | Barbagli et al. |
| 10,478,254 B2 | 11/2019 | Krimsky et al. |
| 10,480,926 B2 | 11/2019 | Froggatt et al. |
| 10,506,946 B2 | 12/2019 | Byrd et al. |
| 10,517,505 B2 | 12/2019 | Morgan et al. |
| 10,524,693 B2 | 1/2020 | Freysinger et al. |
| 10,524,866 B2 | 1/2020 | Srinivasan et al. |
| 10,537,392 B2 | 1/2020 | Millahn et al. |
| 10,551,206 B2 | 2/2020 | Suzuki |
| 10,555,788 B2 | 2/2020 | Panescu et al. |
| 10,569,071 B2 | 2/2020 | Harris et al. |
| 10,575,907 B2 | 3/2020 | Dekel et al. |
| 10,582,879 B2 | 3/2020 | Glossop |
| 10,593,052 B2 | 3/2020 | Abhari et al. |
| 10,603,106 B2 | 3/2020 | Weide et al. |
| 10,603,118 B2 | 3/2020 | Srimohanarajah et al. |
| 10,610,306 B2 | 4/2020 | Chopra |
| 10,615,500 B2 | 4/2020 | Morgan et al. |
| 10,617,324 B2 | 4/2020 | Hunter et al. |
| 10,631,935 B2 | 4/2020 | Amit |
| 10,638,952 B2 | 5/2020 | Morgan et al. |
| 10,638,953 B2 | 5/2020 | Duindam et al. |
| 10,639,114 B2 | 5/2020 | Schuh et al. |
| 10,646,284 B2 | 5/2020 | Weingarten et al. |
| 10,667,679 B2 | 6/2020 | Higgins et al. |

(56) References Cited

U.S. PATENT DOCUMENTS

| | | | |
|---|---|---|---|
| 10,674,936 B2 | 6/2020 | Averbuch et al. |
| 10,674,970 B2 | 6/2020 | Averbuch et al. |
| 10,682,070 B2 | 6/2020 | Duindam |
| 10,702,137 B2 | 7/2020 | Deyanov |
| 10,706,543 B2 | 7/2020 | Donhowe et al. |
| 10,709,506 B2 | 7/2020 | Coste-Maniere et al. |
| 10,772,485 B2 | 9/2020 | Schlesinger et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,885,630 B2 | 1/2021 | Li et al. |
| 11,877,806 B2 * | 1/2024 | Kopel ............... A61B 5/08 |
| 2002/0147462 A1 | 10/2002 | Mair et al. |
| 2003/0013972 A1 | 1/2003 | Makin |
| 2004/0120981 A1 | 6/2004 | Nathan |
| 2008/0045938 A1 | 2/2008 | Weide et al. |
| 2013/0303945 A1 | 11/2013 | Blumenkranz et al. |
| 2014/0035798 A1 | 2/2014 | Kawada et al. |
| 2015/0148690 A1 | 5/2015 | Chopra et al. |
| 2015/0265368 A1 | 9/2015 | Chopra et al. |
| 2016/0157939 A1 | 6/2016 | Larkin et al. |
| 2016/0183841 A1 | 6/2016 | Duindam et al. |
| 2016/0192860 A1 | 7/2016 | Allenby et al. |
| 2016/0287344 A1 | 10/2016 | Donhowe et al. |
| 2017/0112411 A1 | 4/2017 | Costello et al. |
| 2017/0112571 A1 | 4/2017 | Thiel et al. |
| 2017/0112576 A1 | 4/2017 | Coste-Maniere et al. |
| 2017/0209071 A1 | 7/2017 | Zhao et al. |
| 2017/0265952 A1 | 9/2017 | Donhowe et al. |
| 2017/0311844 A1 | 11/2017 | Zhao et al. |
| 2017/0319165 A1 | 11/2017 | Averbuch |
| 2018/0078318 A1 | 3/2018 | Barbagli et al. |
| 2018/0144092 A1 | 5/2018 | Flitsch et al. |
| 2018/0153621 A1 | 6/2018 | Duindam et al. |
| 2018/0235709 A1 | 8/2018 | Donhowe et al. |
| 2018/0240237 A1 | 8/2018 | Donhowe et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0038365 A1 | 2/2019 | Soper et al. |
| 2019/0065209 A1 | 2/2019 | Mishra et al. |
| 2019/0110839 A1 | 4/2019 | Rafii-Tari et al. |
| 2019/0175062 A1 | 6/2019 | Rafii-Tari et al. |
| 2019/0175799 A1 | 6/2019 | Hsu et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192234 A1 | 6/2019 | Gadda et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0239723 A1 | 8/2019 | Duindam et al. |
| 2019/0239831 A1 | 8/2019 | Chopra |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269818 A1 | 9/2019 | Dhanaraj et al. |
| 2019/0269819 A1 | 9/2019 | Dhanaraj et al. |
| 2019/0272634 A1 | 9/2019 | Li et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0336238 A1 | 11/2019 | Yu et al. |
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0030044 A1 | 1/2020 | Wang et al. |
| 2020/0030461 A1 | 1/2020 | Sorger |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0054408 A1 | 2/2020 | Schuh et al. |
| 2020/0060771 A1 | 2/2020 | Lo et al. |
| 2020/0069192 A1 | 3/2020 | Sanborn et al. |
| 2020/0077870 A1 | 3/2020 | Dicarlo et al. |
| 2020/0078023 A1 | 3/2020 | Cedro et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0109124 A1 | 4/2020 | Pomper et al. |
| 2020/0129045 A1 | 4/2020 | Prisco |
| 2020/0129239 A1 | 4/2020 | Bianchi et al. |
| 2020/0138514 A1 | 5/2020 | Blumenkranz et al. |
| 2020/0138515 A1 | 5/2020 | Wong |
| 2020/0142013 A1 | 5/2020 | Wong |
| 2020/0155116 A1 | 5/2020 | Donhowe et al. |
| 2020/0155232 A1 | 5/2020 | Wong |
| 2020/0170623 A1 | 6/2020 | Averbuch |
| 2020/0170720 A1 | 6/2020 | Ummalaneni |
| 2020/0179058 A1 | 6/2020 | Barbagli et al. |
| 2020/0188021 A1 | 6/2020 | Wong et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0229679 A1 | 7/2020 | Zhao et al. |
| 2020/0242767 A1 | 7/2020 | Zhao et al. |
| 2020/0275860 A1 | 9/2020 | Duindam |
| 2020/0297442 A1 | 9/2020 | Adebar et al. |
| 2020/0315554 A1 | 10/2020 | Averbuch et al. |
| 2020/0330795 A1 | 10/2020 | Sawant et al. |
| 2020/0352427 A1 | 11/2020 | Deyanov |
| 2020/0364865 A1 | 11/2020 | Donhowe et al. |
| 2020/0383750 A1 | 12/2020 | Kemp et al. |
| 2021/0000524 A1 | 1/2021 | Barry et al. |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 A | 12/2008 |
| CZ | 486540 B1 | 9/2016 |
| CZ | 2709512 B6 | 8/2017 |
| CZ | 2884879 B1 | 1/2020 |
| EP | 1644519 B1 | 12/2008 |
| EP | 2141497 A1 | 1/2010 |
| EP | 2963616 A2 | 1/2016 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | PA03005028 A | 1/2004 |
| MX | PA03000137 A | 9/2004 |
| MX | PA03006874 A | 9/2004 |
| MX | 225663 B | 1/2005 |
| MX | 226292 B | 2/2005 |
| MX | PA03010507 A | 7/2005 |
| MX | PA05011725 A | 5/2006 |
| MX | 06011286 A | 3/2007 |
| MX | 246862 B | 6/2007 |
| MX | 2007006441 A | 8/2007 |
| MX | 265247 B | 3/2009 |
| MX | 284569 B | 3/2011 |

* cited by examiner

DEFORMABLE REGISTRATION OF COMPUTER-GENERATED AIRWAY MODELS TO AIRWAY TREES

INTRODUCTION

Minimally-invasive surgical (MIS) procedures are a common method of performing various diagnostic and/or treatment procedures on a patient. Among other benefits, MIS procedures pose lower risks and shorter recovery times to the patient relative to other surgical procedures. One MIS procedure, Endobronchial Navigation Bronchoscopy (ENB), involves inserting a bronchoscope and various catheters into a patient's airways to navigate one or more tools to a treatment site to perform a diagnostic and/or treatment procedure. ENB is an effective procedure for accessing areas of the patient's lungs and surrounding parenchyma while minimizing injury to the patient.

Various systems, devices, and computer-implemented methods have been developed to provide image guidance to assist the clinician in identifying the location of the tools in the patient's airways. One such system includes generating one or more three-dimensional (3D) models of the patient's airways based on image data of the patient's chest and displaying a determined location of the tools on the 3D models.

SUMMARY

Provided in accordance with embodiments of the disclosure are methods for registering a luminal network to a 3D model of the luminal network. The method includes receiving location data associated with a location sensor on a tool. The tool navigates the luminal network. The method also includes identifying potential matches in the 3D model with the location data and assigning one of the potential matches a registration score based on a deformation model applied to the 3D model. The method further includes displaying the potential match having a highest registration score.

In another aspect of the disclosure, the assigning of the registration score is further based on a distance between the potential match and the location data, and/or a difference in direction between location sensor direction data and a direction of the potential match.

In a further aspect of the disclosure, the method also includes, after receiving further location data, reassigning the potential match an updated registration score based on the further location data.

In yet another aspect of the disclosure, anchor points from the initial lumen registration are used to constrain the registration.

In another aspect of the disclosure, potential matches assigned a low registration score are discarded.

In a further aspect of the disclosure, the method also includes delaying discarding potential matches with low registration scores when the potential matches are in a bifurcation area of the 3D model.

In yet another aspect of the disclosure, the method further includes updating the 3D model with a plurality of potential matches having the highest registration score.

In another aspect of the disclosure, the deformation model includes identifying a first region of the luminal network and a second region of the luminal network. The deformation model may further include modeling at least one of rotation, compression, extension, and bending for the first region and the second region independently. The deformation model may also include modeling at least one of rotation, compression, extension, and bending for the first region and the second region with adjacent regions having interdependence. The deformation model may include performing rigid registration of the first and second regions to form first and second rigid registrations and stitching together the first and second rigid registrations.

In a further aspect of the disclosure the luminal network is a bronchial airway, and the deformation model includes applying a moving window from a trachea to a periphery of the bronchial airway. The method may include performing a rigid registration in the moving window.

In another aspect of the disclosure, the deformation model may include weighing registration for central areas of the lungs greater than peripheral areas of the lungs or using deformation models having different deformation characteristics for at least one of a right lung, a left lung, and each lung lobe. The deformation model may include using a biomechanical model of the lungs based on finite image analysis, using a deformation model based on a specific disease, and/or using at least one of a bronchoscope model and a catheter model to produce a specific deformation model.

Embodiments of the disclosure also provide a system for updating a 3D model of a luminal network. The system includes a location sensor capable of being navigated within a luminal network inside a patient's body. The system further includes an EM navigation system including an EM field generator configured to generate an EM field, and an EM tracking system configured to detect a location of the EM sensor within the EM field. The system also includes a computing device including a processor and a memory storing instructions. The instructions, when executed by the processor, cause the computing device to receive location data associated with a location sensor on a tool. The tool navigates the luminal network. The instructions further cause the computing device to identify a plurality of potential matches in the 3D model with the location data and assign at least one of the potential matches a registration score based on a deformation model applied to the 3D model. The instructions also cause the computing device to display the potential match having a highest registration score.

A further aspect of the disclosure is directed to a method of registering a 3D model to a luminal network. The method includes generating a 3D model of a luminal network from a pre-procedure image data set, conducting a survey of the luminal network, generating a 3D model of the luminal network from data captured during the survey, and applying a transform to the 3D model of the luminal network generated from the pre-procedure image data set to approximate the 3D model of the luminal network generated from the data captured during the survey.

In accordance with further aspects of the disclosure, the survey data is collected with a sensor inserted into each lobe of a lung of a patient. Further, the sensor may be an electromagnetic sensor collecting electromagnetic position data. Still further aspects of the disclosure include applying a plurality of transforms to the 3D model of the luminal network generated from the pre-procedure image data set. The transform may be selected by determining which of a plurality of transforms result in a best fit of the 3D model generated from the pre-procedure image data to the 3D model from the data captured during the survey.

Any of the above aspects and embodiments of the disclosure may be combined without departing from the scope of the disclosure.

BRIEF DESCRIPTION OF THE DRAWINGS

Various aspects and features of the disclosure are described hereinbelow with references to the drawings, wherein.

DETAILED DESCRIPTION

The disclosure is directed to devices, systems, methods, and computer-readable media for registering a 3D bronchial tree model (hereinafter referred to as a "3D model") with a patient's airways based on electromagnetic navigation.

There is a continuing need for systems and methods that accurately register 3D models to the patient's actual airways. Since lungs are flexible, dynamic, and deformable organs, there is usually a significant, dynamic difference between the bronchial tree of the patient during a procedure and the bronchial tree in the CT/MRI image or model.

As such, the systems and methods discussed herein accommodate the flexibility and elasticity of the lungs using a set of registration methods.

During ENB procedures, it is important to register the magnetic navigation space to the patient's CT scan. As understood in the art, "registration" refers to a translation, mapping, transformation, or the like, which converts locations or coordinates in one space to locations or coordinates in another space. In order to perform such registration, several methods have been developed. One method, known as manual registration, is based on the visual identification of the bronchoscope with the main airway's branching points and associating them with the points visually identified on the CT scans. During the ENB procedure, the user navigates the bronchoscope with a catheter fitted with the magnetic sensing coil to the branching points in the airways, and manually generates the associations between the branching points and the locations in the magnetic navigation space. Another method, known as automatic registration, is based on collection of the point cloud from the airways (called survey) using a catheter with the magnetic sensor at its tip, and then fitting the survey to the image of the airway tree derived from the CT scan using a suitable image segmentation algorithm.

Due to the flexibility of the lungs, the actual shape of the lungs during the time of a surgical procedure can be deformed or different from the shape at the time of the CT scan and/or initial registration, resulting in the reduction of navigation accuracy. This deformation caused by the flexibility of the lungs may be due to several differences, such as: (1) the CT scan being performed while the patient is holding their breath after a full inhale, whereas during the surgical procedure, both registration and navigation, the patient is sedated and breathing normally; (2) the patient may be horizontal for a much longer period during the surgical procedure thereby causing increased deformation; (3) during the surgical procedure, while the bronchoscope is inside of the patient, the head, neck, and superior part of the chest may also be deformed; and/or (4) the CT scan being performed on a concave bed, as is typical, while the surgical procedure is generally performed while the patient is lying flat.

In navigational bronchoscopy (for example electromagnetic navigation bronchoscopy, also referred to as ENB) systems, rigid or semi-rigid algorithms are often used to map the intra-procedural bronchial tree or airway carinas to the bronchial tree or airway carinas in a CT scan. However, because the lungs are flexible, dynamic, and deformable organs, there is usually a significant, dynamic difference between the bronchial tree of the patient during a procedure and the bronchial tree in the CT scan. While described in the disclosure as a CT scan, other suitable imaging modalities such as, for example, MRI, may be used to generate image data (e.g., MRI scan) of the bronchial tree or airway carinas.

The bronchial tree deforms due to respiration, changes in patient position, the force applied by the bronchoscope and other endoscopic tools, and other reasons. The deformation is different for each patient and can be significantly different for the same patient on different occasions. Therefore, it is difficult to estimate with sufficient accuracy how the lungs will deform from the time of the CT scan to the time of the procedure. However, it has been empirically shown that certain deformations are more probable than others. In order to utilize this information to provide more accurate registration, these deformations are modeled. Deformable registration includes aligning the virtual bronchial tree to a 3D model of the bronchial tree obtained through a CT scan. Each branch is aligned independently, and/or certain deformations are deemed more reasonable and others less reasonable.

Any such model has a "registration score" or "likelihood score" which is higher for more likely deformations and lower for less likely deformations. Regional deformation models can have this score, or confidence interval, based on what happens in other areas, for instance adjacent areas, and the deformation model may be selected based on the best score. Additionally, the model score could be affected by type and/or characteristic of the tool used.

Lungs, lobes, segments, airways or other regions in the lung can be modeled to rotate independently of each other, extend, compress, or bend. The likelihood of a particular deformation may be considered identical for the entire lungs or may change depending on bifurcation generation, inserted catheter, and other parameters. Deformation in a specific lung, lobe, segment, or airway can be modeled to affect potential deformations in sub-regions or neighboring lung regions. For example, if the right main bronchus has extended 20%, it may be more likely that the intermediate bronchus has extended as well.

The lungs may be divided into multiple arbitrary or anatomical regions. In each region, a rigid registration is performed, and then all registrations may be smoothly "stitched" into a single model or image. This process includes separately registering regions based on regional models, which may be different, and then smoothly aligning the multiple registrations. Smoothing may be accomplished using a suitable image stitching algorithm.

A moving window may be applied from the trachea to the periphery of the lung. Within each window, a rigid registration may be performed. Thus, deformation may progressively increase as the image approaches the periphery of the lung.

In the periphery of the lungs, confidence in registration is reduced by factors such as, for example, small and close airways, respiration, missing branches in the segmented bronchial tree, and limited surveys. Therefore, regardless of the deformation model that is used, deformations in the central area of the lungs generally may be trusted more. In addition, if a certain local deformation is not very likely, but there are no other more likely candidates, then this deformation can also be trusted more than if alternative deformations were a possibility.

There could be different deformation characteristics for the right and left lung and/or for each of the lung lobes or segments. For example, it may be empirically shown that the lateral basal segments are often rotated to the right, while apical segments compress.

Various biomechanical models of the lungs may be used, including, for example, models based on finite image analysis. These models may be utilized for predicting respiratory movement during radiotherapy. The use of these models could be expanded to provide deformable registration for ENB. Certain diseases such as emphysema or various lung lesions and tumors can be modeled to produce specific local or global deformations. Different bronchoscope and catheters models can be modeled to produce specific deformations. Deformation can depend on the mechanical properties of the endoscopic tool, its flexion or orientation relative to the airway wall, the diameter and stiffness of the airway, the direction of motion (forward or backward), the position of the tool relative to a bifurcation, and other variables.

Causes for divergence from the CT scan to the patient's body can be modeled separately and then combined. For example, a certain patient position during CT scan and a different position during the ENB procedure (hands up/down, etc.) may be modeled. A different bed curvature in the CT scanner than in the ENB procedure bed may also be modeled. The application of force by the bronchoscope and catheter on the airway walls may be modeled. Sedation, anesthesia, and/or muscle blockers have an effect on lung anatomy, which may be modeled. Likewise, a change in patient anatomy from the time of the CT scan may impact registration, and may also be modeled (e.g., changes caused by the development of pneumonia, a change in weight, etc.). In computing the divergence, the minimum distance from each survey point to a prospective transformation of the reference airway tree may be multiplied by the weight assigned to the corresponding survey point, and the weighted minimum distances are averaged. This process for a particular region is referred to as optimized region registration.

Still other causes for changes in airway pathways include full inhalation during CT scan and tidal respiration cycle during ENB procedure, coughing, non-rigid patient movement during ENB procedure, and change in respiration patterns during the procedure. Each of these actions may be modeled and utilized in accordance with aspects of the disclosure.

A registration method is proposed that may use any of the deformation models described, any combination of them, or any other model, as long as the model can be empirically validated and the likelihood for each modeled deformation (referred to as a registration score) can be deduced. For example, it is less probable for an airway to extend twice in size from the time of the CT scan to the time of the ENB procedure than for it to extend only 10%. Therefore, the probability of extension can be modeled to decrease with increase in degree of extension.

During an ENB procedure, the system uses the registration and/or navigation samples to track catheter/bronchoscope/tool movement in the airways such that each sample can be matched to a specific point in the bronchial tree. This matching is based on the selected deformation model. Conventional lumen registration methods attempt to find a match such that the mean distance between the survey and the bronchial tree is minimal. The conventional methods don't utilize the fact that the survey has to be continuous and follow a certain path through the lungs. Therefore, conventional registration methods may match neighbor samples to completely separate segments in the lung, which reduces accuracy of registration. In contrast, the proposed method of the disclosure follows the route of the tracked tool, sample by sample, from the trachea to other regions in the lung, thereby ensuring that a logical path is being followed. Before samples are matched, filters that dilute the samples, remove outliers, and/or reduce respiration noise can be applied. Due to performance considerations, a more detailed model can be used for samples of interest and a rougher model can be used for other samples.

Since, using a given deformation model, there are usually multiple ways to match samples to the bronchial tree, the system selects those matches in which the series of deformations that produce the match is most probable according to the model. For example, a deformation in which the right upper lobe has rotated 20 degrees relative to the right main bronchus has a higher probability than a series of deformations in which all five lobes have rotated 15 degrees. A registration is then created based on the selected match. Depending at least in part on the deformation model, the registration can be flexible, such as a thin plate spline, it can consist of multiple rigid registrations, one for each deformed region, or it can include a different registration for each sample. The system may store in memory the top matches, so that if a new sample or samples are received during navigation, the system can update the top matches and avoid re-computing all possible matches, many of which may be improbable.

Figure 5:
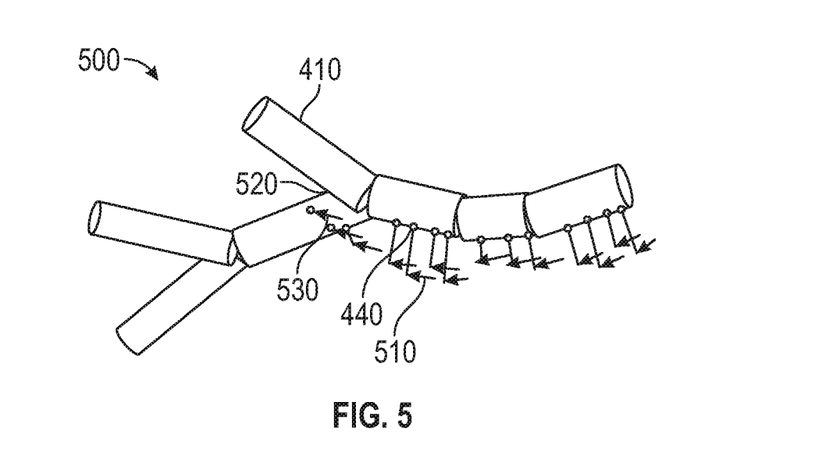
FIG. 5 shows a lumen registration in which the system matches new samples to an airway of the 3D model.

An example of a detailed implementation follows. A lumen registration is performed. For each new navigation sample received by the system, the system tries to match the sample to the most likely airways in the bronchial tree. (see FIG. 5, illustrating a match). This operation is performed for each active match.

Figure 6A:
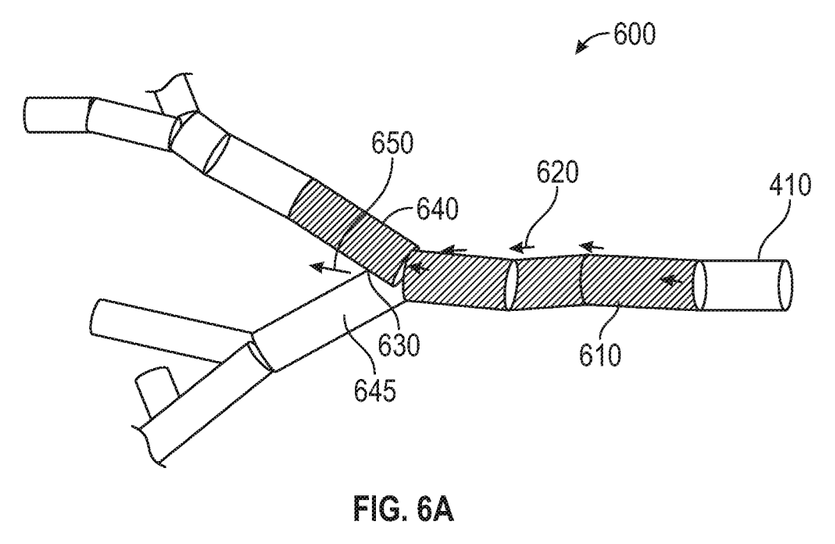
FIGS. 6A-6D illustrate registration with a 3D model before and after branching of the bronchial airway.
Figure 6B:
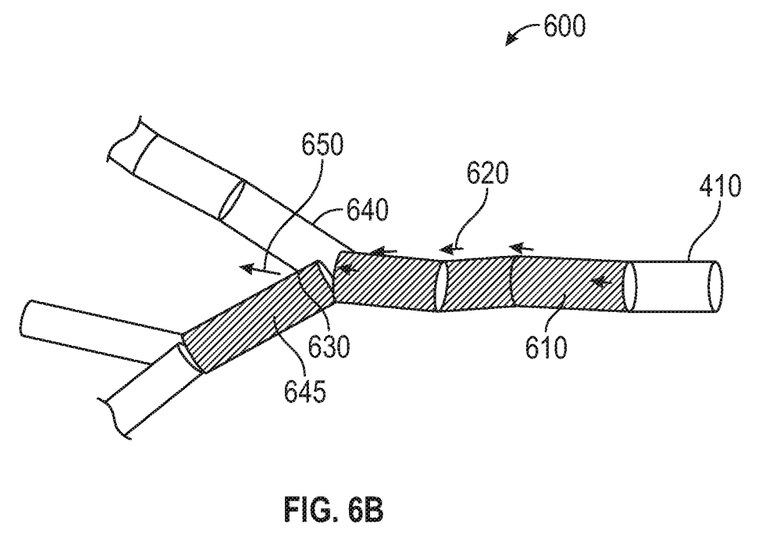
Figure 6C:
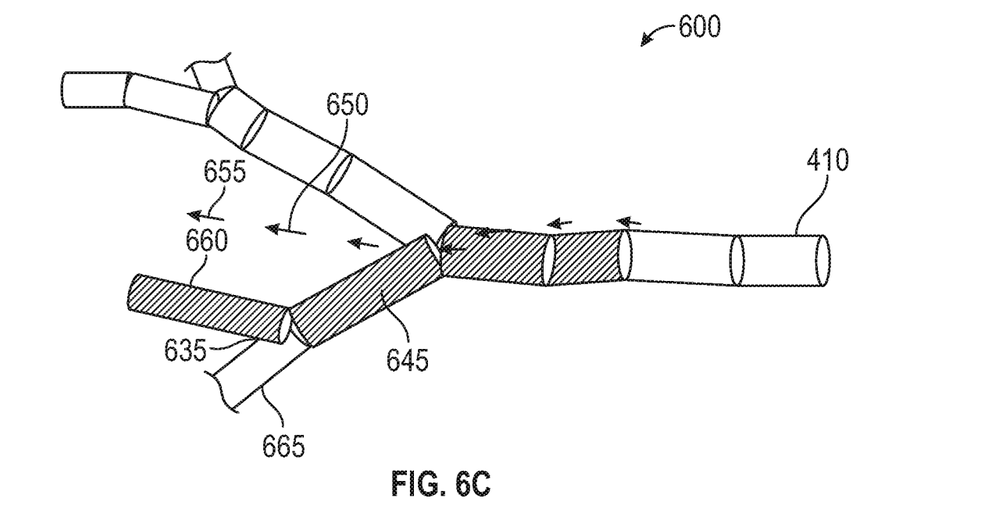
Figure 6D:
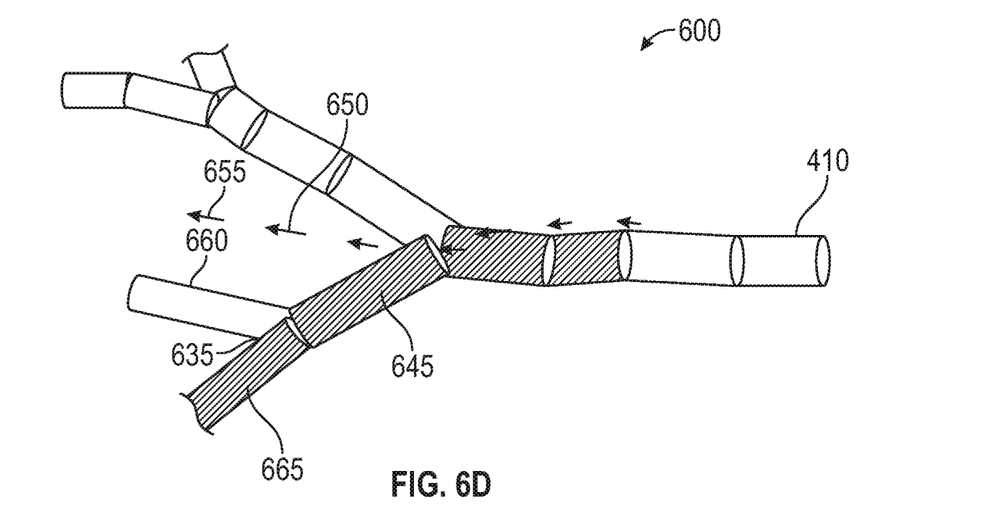

If multiple matches are likely, each match is evaluated and tracked independently throughout navigation (see FIGS. 6A-6B, illustrating branching). After subsequent navigation, each match can be split further to multiple matches (see FIGS. 6C-6D, illustrating further branching). Each active match is evaluated for fit by calculating the distance of the samples to the matched bronchial path (both position and orientation are used). Identification of a bifurcation depends on the angle between branches and/or the length of each branch.

Figure 4:
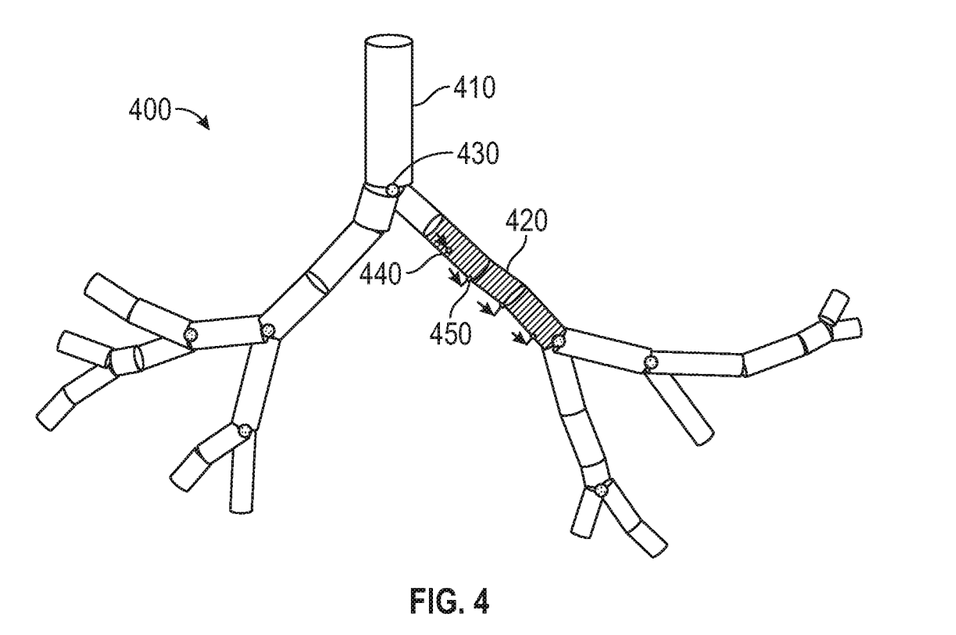
FIG. 4 shows an exemplary 3D model of a bronchial airway including sensor data.

In addition, anchor points from the initial lumen registration are used to constrain the registration (see FIG. 4, illustrating registration). Constraining registration avoids excessive flexibility in the registration process. For example, certain lobes can move by some amount, but some lobes may only stretch, and others only compress. Additionally, the lobes deformability may be interdependent. For example, if one region stretches 20%, other region may compress 15%, or move and/or rotate in a similarly constrained fashion.

Figure 7:
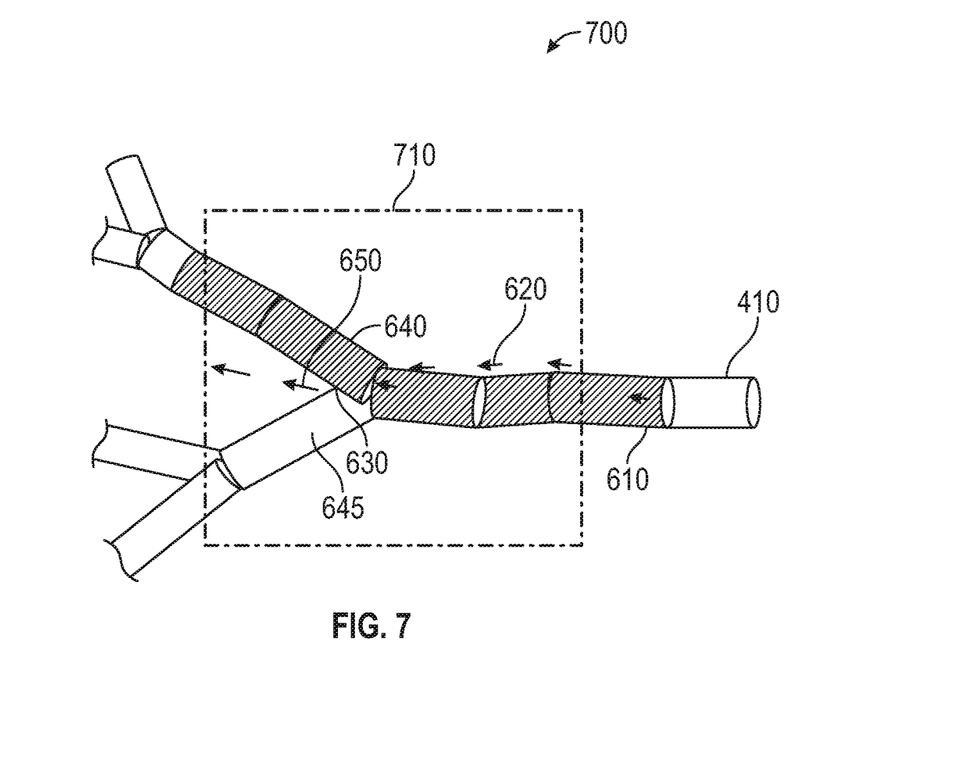
FIG. 7 shows a lumen registration performed using a moving boundary box.

Significantly unfit matches are discarded. The fittest match is selected to be used for final display of the endoscopic tool on a CT scan image. As new navigation samples are acquired, old navigation samples are discarded in order to allow deformability (see FIG. 7, illustrating bounding box). This bounding box may move with the catheter or other tool and may define a zone in which rigid registration is performed. In this manner, the model may be rigid in localized regions, but deform outside that region by virtue of the flexibility of the alignment between the different rigid registrations. Outlier samples may be discarded assuming cough or tissue deformation by the catheter. Bifurcation areas are treated differently by delaying the splitting of the match until further matches are acquired. Transitions between branches are smoothed to better represent real anatomy. Outside of the bronchial tree, a more conservative recent correction is used.

In some embodiments, image data may be acquired to generate, and be displayed in conjunction with or alongside, a digital reconstruction, such as a three-dimensional (3D) model or map, of the patient's lungs or another portion of the patient's body. Various imaging modalities may be used to acquire the image data, including computed tomography (CT) imaging, cone beam computed tomography (CBCT) imaging, magnetic resonance (MR) imaging, positron emission tomography (PET) imaging, fluoroscopic imaging, X-ray imaging, and/or ultrasound imaging. The 3D model may be constructed based on preoperative image data from one or more of the aforementioned imaging modalities. Alternatively or additionally, additional image data, such as from a CBCT scan, may be acquired at the start of the treatment procedure and be used for registration purposes, as further described below, and for constructing and/or enhancing the 3D model.

To create the 3D model, a preoperative segmental and subsegmental delineation and extrapolation may be performed based on image data of the patient's lungs to create a visual representation of the patient's lungs. The visual representation may include lumens, pleural surfaces, and fissures of the patient's lungs, and/or tumors or other aberrant structures that may be present in the patient's lungs. The delineation may be performed using one or more software applications executing on a computer. The application may generate the 3D model of the patient's lungs based on the image data, noted above, to use for the visual representation of the patient's lungs. The 3D model and image data may then be viewed by a clinician and/or surgeon to plan a medical treatment procedure, such as a surgical or interventional procedure. The 3D model and/or treatment plan may further be stored for later viewing during the treatment procedure in an operating room or the like.

As described further below, the treatment plan may include identified locations for one or more treatment targets, such as tumors, lesions, or other aberrant structures identified in the image data, and a pathway between the patient's trachea and each of the treatment targets. The pathway may include a portion located inside lumens, such as airways, of the patient's lungs, and a portion located outside of the airways of the patient's lungs. An "exit point" may mark the transition point between the portion of the pathway located inside the patient's airways and the portion of the pathway located outside of the patient's airways.

During the treatment procedure, the 3D model may be displayed, as further described below, to assist the clinician in navigating one or more tools to the treatment target. The 3D model may include an indicator of a tracked position of the tool inside the patient's lungs. At various times during the treatment procedure, additional image data may be acquired, such as by performing additional CBCT scans, to show a real-time location of the tool and/or the treatment target in the patient's lungs. For example, after the tool passes the "exit point" and is located outside of the patient's airways, or at any other time of the clinician's choosing, additional image data may be acquired and processed to identify the tool and/or the treatment target. The indicator on the 3D model of the tracked position of the tool may then be updated based on the additional image data, thereby showing a confirmed location of the tool and/or the treatment target. The additional image data may further show, and thus enable a software application with the ability to track, the location of the tool during various phases of the patient's respiration cycle. While the 3D model may be generated based on image data acquired while the patient was in a particular phase of the respiration cycle, e.g. full breath hold, the patient will not remain in that phase of the respiration cycle for the entire duration of the treatment procedure. Thus, acquiring image data during the treatment procedure during various phases of the patient's respiration cycle, particularly during normal tidal volume breathing, may provide a clearer and more accurate visualization of the location of the tool and the treatment target inside the patient's lungs, as well as the position of the tool relative to the treatment target.

Further, as will be appreciated by those skilled in the art, the devices, systems, and methods described herein may also be used during other types of medical procedures, such as percutaneous and/or laparoscopic procedures, involving placement of a tool at a treatment site under image-guided and/or electromagnetic (EM) systems. As such, the illustrative embodiments described below are merely provided as examples and are not intended to be limiting.

An electromagnetic navigation (EMN) system may be used for planning and performing treatment of an area of a patient's lungs. Generally, in an embodiment, the EMN system may be used in planning treatment of an area of the patient's lungs by identifying the positions of one or more treatment targets in the patient's lungs, selecting one or more of the treatment targets as a target location, determining a pathway to the target location, navigating a positioning assembly to the target location, and navigating a variety of tools to the target location via the positioning assembly. The EMN system may be configured to display various views of the patient's lungs, including the aforementioned image data and 3D model.

Figure 1:
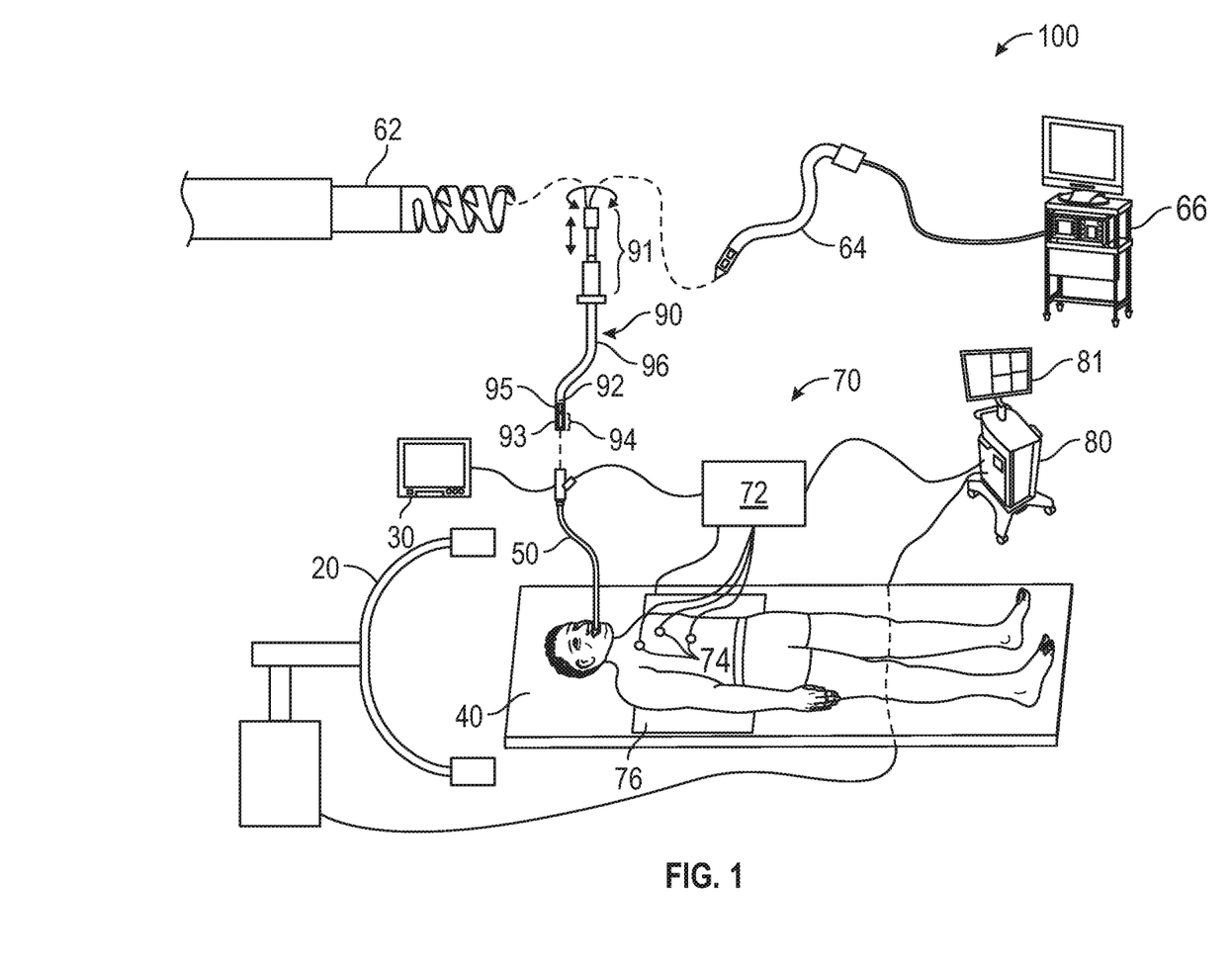
FIG. 1 is a schematic diagram of an endobronchial system for planning and performing treatment of an area of a patient's lungs.

FIG. 1 illustrates an EMN system 100 suitable for implementing methods for detecting tool displacement during medical procedures. EMN system 100 is used to perform one or more procedures on a patient supported on an operating table 40 and generally includes monitoring equipment 30 (e.g., video and/or image display), a bronchoscope 50, an EM tracking system 70, and a computing device 80.

Bronchoscope 50 is configured for insertion through the patient's mouth and/or nose into the patient's airways. Bronchoscope 50 includes a source of illumination and a video imaging system (not explicitly shown) and is coupled to monitoring equipment 30 for displaying the video images received from the video imaging system of bronchoscope 50. In an embodiment, bronchoscope 50 may operate in conjunction with a catheter guide assembly 90. Catheter guide assembly 90 includes a catheter 96 configured for insertion through a working channel of bronchoscope 50 into the patient's airways (although the catheter guide assembly 90 may alternatively be used without bronchoscope 50). Catheter guide assembly 90 further includes a handle 91 connected to catheter 96, and which can be manipulated by rotation and compression to steer catheter 96 and/or tools inserted through catheter 96, such as a locatable guide (LG) 92. catheter 96 is sized for placement into the working channel of bronchoscope 50. In the operation of catheter guide assembly 90, LG 92, including an EM sensor 94, is inserted into catheter 96 and locked into position such that EM sensor 94 extends a desired distance beyond a distal tip 93 of EWC 96. In some embodiments, catheter 96 may also include or have coupled thereto an EM sensor 95, and the EM sensors 94, 95 may alternately or collectively be used to determine the position of and steer catheter 96 and/or tools inserted therein. The location of EM sensors 94, 95, and thus distal tip 93 of catheter 96, within an EM field generated by EM field generator 76, can be derived by tracking module 72 and computing device 80.

LG 92 and catheter 96 are selectively lockable relative to one another via a locking mechanism. A six degrees-of-freedom EM tracking system 70, or any other suitable positioning measuring system, is utilized for performing navigation, although other configurations are also contemplated. Though sensors 94 and 95 are described herein as EM sensors, the disclosure is not so limited. The sensors 94 and 95 may be flexible sensors, such as fiber brag grating sensors, which can be used to determine the flex and orientation of the catheter 96, or other sensors including ultrasound sensors, accelerometers, temperature sensors, and others without departing from the scope of the disclosure.

EM tracking system 70 may be configured for use with catheter guide assembly 90 to track a position of EM sensors 94, 95 as they move in conjunction with catheter 96 through the airways of the patient. In an embodiment, EM tracking system 70 includes a tracking module 72, a plurality of reference sensors 74, and an EM field generator 76. As shown in FIG. 1, EM field generator 76 is positioned beneath the patient. EM field generator 76 and the plurality of reference sensors 74 are interconnected with tracking module 72, which derives the location of each reference sensor 74 in the six degrees of freedom. One or more of reference sensors 74 are attached to the chest of the patient. The coordinates of reference sensors 74 are sent as data to computing device 80, which includes an application 81, where the data from reference sensors 74 are used to calculate a patient coordinate frame of reference.

Although EM sensors 94, 95 are described above as being included in LG 92 and catheter 96, respectively, an EM sensor may be embedded or incorporated within a treatment tool, such as a biopsy tool 62 and/or an ablation tool 64, where the treatment tool may alternatively be utilized for navigation without need of LG 92 or the necessary tool exchanges that use of LG 92 requires.

Treatment tools 62, 64 are configured to be insertable into catheter guide assembly 90 and catheter 96 following navigation to a target location and removal of LG 92 (if used). Biopsy tool 62 may be used to collect one or more tissue samples from the target location, and in an embodiment, is further configured for use in conjunction with tracking system 70 to facilitate navigation of biopsy tool 62 to the target location, and tracking of a location of biopsy tool 62 as it is manipulated relative to the target location to obtain the tissue sample. Ablation tool 64 is configured to be operated with a generator 66, such as a radio frequency generator or a microwave generator and may include any of a variety of ablation tools and/or catheters.

Though shown as a biopsy tool and microwave ablation tool in FIG. 1, those of skill in the art will recognize that other tools, including for example RF ablation tools, brachytherapy tools, cryo-ablation tools, and others may be similarly deployed and tracked without departing from the scope of the disclosure. Additionally, a piercing tool and/or puncture tool may be used and/or incorporated within LG 92 to create an exit point where LG 92, and thereby catheter 96, is navigated outside of the patient's airways and toward the target location.

A radiographic imaging device 20, such as a computed tomography (CT) imaging device, magnetic resonance imaging (MRI) imaging device, positron emission tomography (PET) imaging device, a cone beam computed tomography (CBCT) imaging device such as a C-arm imaging device, and/or any other imaging device capable of performing a scan of at least a portion of the patient's lungs, may be used in conjunction with EMN system 100. Imaging device 20 may further be capable of performing fluoroscopic scans of the patient's lungs. As shown in FIG. 1, imaging device 20 is connected to computing device 80 such that application 81 may receive and process image data obtained by imaging device 20. However, imaging device 20 may also have a separate computing device located within the treatment room or in a separate control room to first receive the image data obtained by imaging device 20 and relay such image data to computing device 80. For example, to avoid exposing the clinician to unnecessary radiation from repeated radiographic scans, the clinician may exit the treatment room and wait in an adjacent room, such as the control room, while imaging device 20 performs the scan.

Computing device 80 includes software and/or hardware, such as application 81, used to facilitate the various phases of an EMN procedure, including generating a 3D model, identifying a target location, planning a pathway to the target location, registering the 3D model with the patient's actual airways, navigating to the target location, and performing treatment at the target location. For example, computing device 80 utilizes data acquired from a CT scan, CBCT scan, MRI scan, PET scan, and/or any other suitable imaging modality to generate and display the 3D model of the patient's airways, to enable identification of a target location on the 3D model (automatically, semi-automatically or manually) by analyzing the image data and/or 3D model, and allow for the determination and selection of a pathway through the patient's airways to the target location. The 3D model may be presented on a display monitor associated with computing device 80, or in any other suitable fashion.

Using computing device 80, various views of the image data and/or 3D model may be displayed to and manipulated by a clinician to facilitate identification of the target location. The target location may be a site within the patient's lungs where treatment is to be performed. For example, the treatment target may be located in lung tissue adjacent to an airway. The 3D model may include, among other things, a model airway tree corresponding to the actual airways of the patient's lungs, and show the various passages, branches, and bifurcations of the patient's actual airway tree. Additionally, the 3D model may include representations of lesions, markers, blood vessels and vascular structures, lymphatic vessels and structures, organs, other physiological structures, and/or a 3D rendering of the pleural surfaces and fissures of the patient's lungs. Some or all of the aforementioned elements may be selectively displayed, such that the clinician may choose which elements should be displayed when viewing the 3D model.

After identifying the target location, application 81 may determine a pathway between the patient's trachea and the target location via the patient's airways. In instances where the target location is located in lung tissue that is not directly adjacent an airway, at least a portion of the pathway will be located outside of the patient's airways to connect an exit point on an airway wall to the target location. In such instances, LG 94 and/or catheter 96 will first be navigated along a first portion of the pathway through the patient's airways to the exit point on the airway wall. LG 94 may then be removed from catheter 96 and an access tool, such as a piercing or puncture tool, inserted into catheter 96 to create an opening in the airway wall at the exit point. catheter 96 may then be advanced through the airway wall into the parenchyma surrounding the airways. The access tool may then be removed from catheter 96 and LG 94 and/or tools 62, 64 reinserted into catheter 96 to navigate catheter 96 along a second portion of the pathway outside of the airways to the target location.

During a procedure, EM sensors 94, 95, in conjunction with tracking system 70, enables tracking of EM sensors 94, 95 (and thus distal tip 93 of catheter 96 or tools 62, 64) as catheter 96 is advanced through the patient's airways following the pathway planned during the planning phase. As an initial step of the procedure, the 3D model is registered with the patient's actual airways to enable application 81 to display an indication of the position of EM sensors 94, 95 on the 3D model corresponding to the location of EM sensors 94, 95 within the patient's airways.

One potential method of registration involves performing a survey of the patient's lungs by navigating LG 92 into each lobe of the patient's lungs to at least the second bifurcation of the airways of that lobe. The position of LG 92 is tracked during this registration phase, and the 3D model is iteratively updated based on the tracked position of LG 92 within the actual airways of the patient's lungs. While the registration process focuses on aligning the patient's actual airways with the airways of the 3D model, registration also ensures that the position of vascular structures, pleural surfaces, and fissures of the lungs are accurately determined. Anchor points 430 (FIG. 4), which may correspond to bifurcation points in the bronchial airway, may be obtained during this initial lumen registration and used to constrain the registration.

Figure 2:
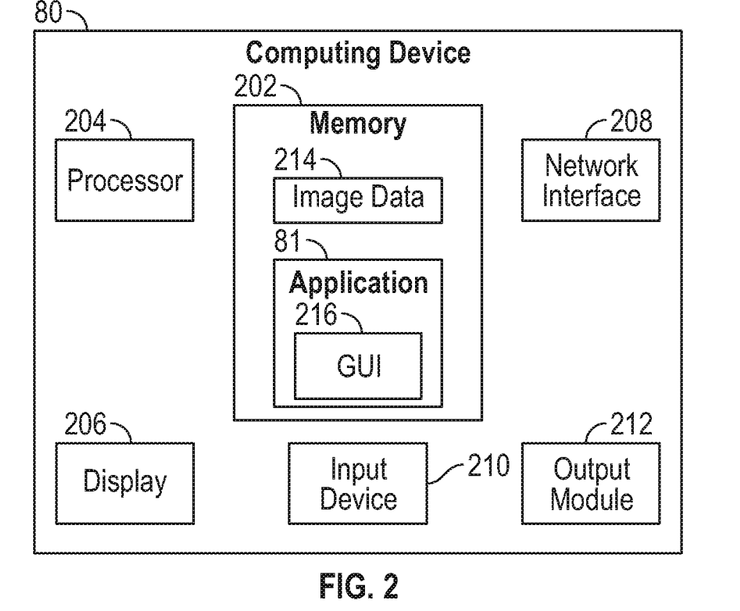
FIG. 2 is a block diagram of an example computing device forming part of the system of FIG. 1.

FIG. 2 illustrates a simplified block diagram of computing device 80. Computing device 80 may include a memory 202, a processor 204, a display 206, a network interface 208, an input device 210, and/or an output module 212. Memory 202 may store application 81 and/or image data 214. Application 81 may include instructions and/or executable code for generating a graphical user interface (GUI) 216 which, when executed by processor 204, cause display 206 to display a GUI.

Memory 202 may include any non-transitory computer-readable storage media for storing data and/or software that is executable by processor 204 and which controls the operation of computing device 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with computing device 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Figure 3:
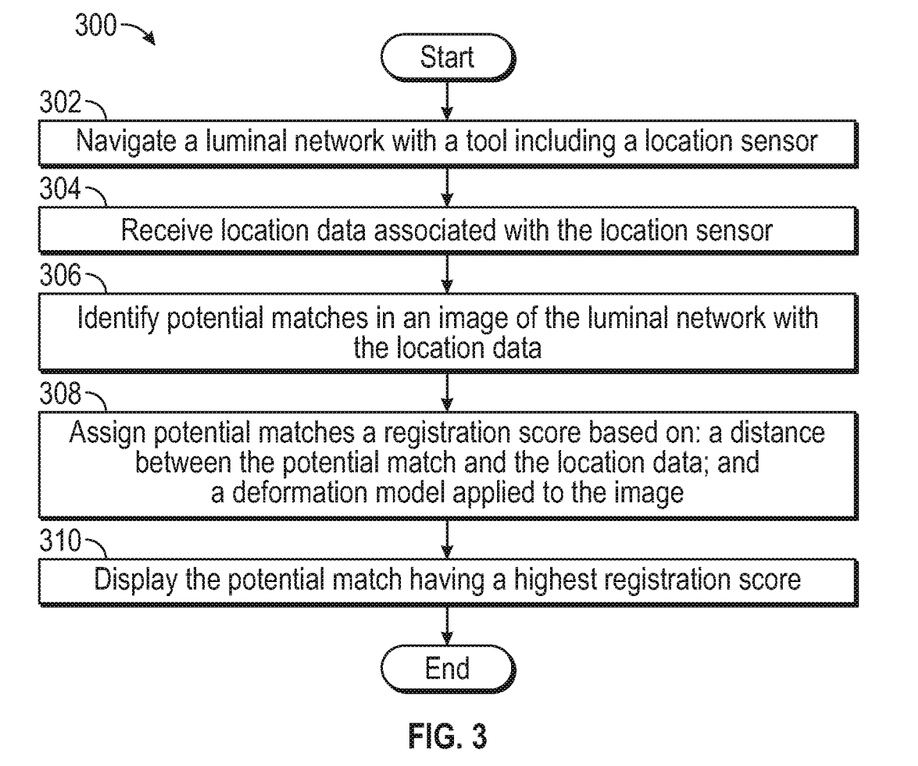
FIG. 3 shows a flowchart of an example method for registering a luminal network to a 3D model of the luminal network.

FIG. 3 is a flow chart illustrating a method 300 for registering a luminal network to a 3D model of the luminal network. Method 300 begins at operation 302, which includes navigating a luminal network with a tool including a location sensor. From operation 302, the flow in method 300 proceeds to operation 304, which includes receiving location data associated with the location sensor. From operation 304, the flow in method 300 proceeds to operation 306, which includes identifying potential matches in an image of the luminal network with the location data. From optional operation 306, the flow in method 300 proceeds to operation 308, which includes assigning potential matches a registration score based on a distance between the potential match and the location data, and a deformation model applied to the image. From operation 308, the flow in method 300 proceeds to operation 310, which includes displaying the potential match having a highest registration score. From operation 310, the flow in method 300 proceeds to the end circle. The order of operations shown in FIG. 3 is exemplary only, and operations may be performed in a different order.

FIG. 4 shows exemplary 3D model 400 of a bronchial airway 410 having a branch 420. Also shown in FIG. 4 are sensor data 440, 450 obtained from a location sensor, for instance an EM sensor on a bronchoscope. Also illustrated in FIG. 4 are anchor points 430, which may correspond to bifurcation points in the bronchial airway 410 forming branches, for instance, branch 420. Anchor points 430 may be obtained during the initial lumen registration and may be used to constrain the registration.

FIG. 5 shows lumen registration 500 in which a system matches new samples to bronchial airway 410 of the 3D model. Registration datum 440 includes both a position and direction 510. Registration datum 530 occurs after bifurcation 520 in bronchial airway 410 and assists in determining into which branch the bronchoscope has traveled.

FIG. 6A illustrates registration using 3D model 600 at a branching of bronchial airway 410. Sensor data 620 includes a position and direction, and the position may be outside initial airway 610. However, based on a deformation model, sensor data 620 may receive a high registration score, and therefore may be considered a best estimate of the position of the location sensor of the bronchoscope. 3D model 600 may be adjusted based on the deformation model. Initial airway 610 may end at bifurcation 630, which may indicate the beginning of branches 640 and 645. Another sensor data 650 may indicate a position beyond bifurcation 630, but between branches 640 and 645. Therefore, the system may give a weighted score assigning sensor data 650 to branch 640.

FIG. 6B illustrates registration according to the disclosure as shown in FIG. 6A, using 3D model 600 at a branching of bronchial airway 410 at bifurcation 630. Sensor data 620 may be registered to initial airway 610, as discussed above. Based on another sensor data 650, the system may not be able to conclude in which of branches 640 and 645 the bronchoscope is traveling, as discussed above, and therefore, the system may give another weighted score assigning sensor data 650 to branch 645.

FIG. 6C illustrates registration according to the disclosure as shown in FIGS. 6A and 6B, using 3D model 600 at a further branching of bronchial airway 410 at bifurcation 635. Based on another sensor data 650 and further sensor data 655, the system may conclude the bronchoscope is traveling down branch 645, and not branch 640. This conclusion may be realized by assigning a higher weighted score to registration with branch 645 than registration with branch 640. Further sensor data 655 may indicate a position beyond bifurcation 635. Therefore, the system may give a weighted score assigning sensor data 650 to branch 660.

FIG. 6D illustrates registration according to the disclosure as shown in FIGS. 6A, 6B, and 6C, using 3D model 600 at a branching of bronchial airway 410 at bifurcation 635. Based on further sensor data 655 being positioned significantly away from branch 665, the system may assign a very low score to registration of further data 655 with branch 665. Additionally or alternatively, the system may identify a larger difference in direction between further sensor data 655 and branch 665 than between further sensor data 655 and branch 660. Consequently, the system may assign a higher registration score to branch 660 based on the difference in direction data. Alternatively, the system may discard all possibilities associated with further data 655 being registered with branch 665. In this manner, branch 660 may arise as the best possible fit for further sensor data 655.

FIG. 7 shows a lumen registration performed in which the system matches new samples to bronchial airway 410 of 3D model 700 within moving boundary box 710. Moving boundary box 710 may move with the position of the location sensor, which may be centered within moving boundary box 710 or may be elsewhere within moving boundary box 710. As the bronchoscope or other tool having the location sensor is moved within bronchial airway 410, moving boundary box 710 may also move. Moving boundary box 710 may move incrementally, or in steps so that successive positions of moving boundary box 710 do not overlap or only overlap slightly. Within moving boundary box 710, the system may perform a first rigid registration between sensor data 620 and 3D model 700, and after moving boundary box 710, a second rigid registration may be performed. Subsequently, the first and second rigid registrations may be stitched together to form a single registration.

In FIG. 7, sensor data 620 includes a position and direction, and the position may be outside initial airway 610. Based on a deformation model, sensor data 620 may receive a high registration score, and therefore may be considered a best estimate of the position of the location sensor of the bronchoscope. 3D model 700 may be adjusted based on the deformation model. Initial airway 610 may end at bifurcation 630, which may indicate the beginning of branches 640 and 645. Another sensor data 650 may indicate a position beyond bifurcation 630, but between branches 640 and 645. Therefore, the system may give a weighted score assigning sensor data 650 to branch 640.

Figure 8:
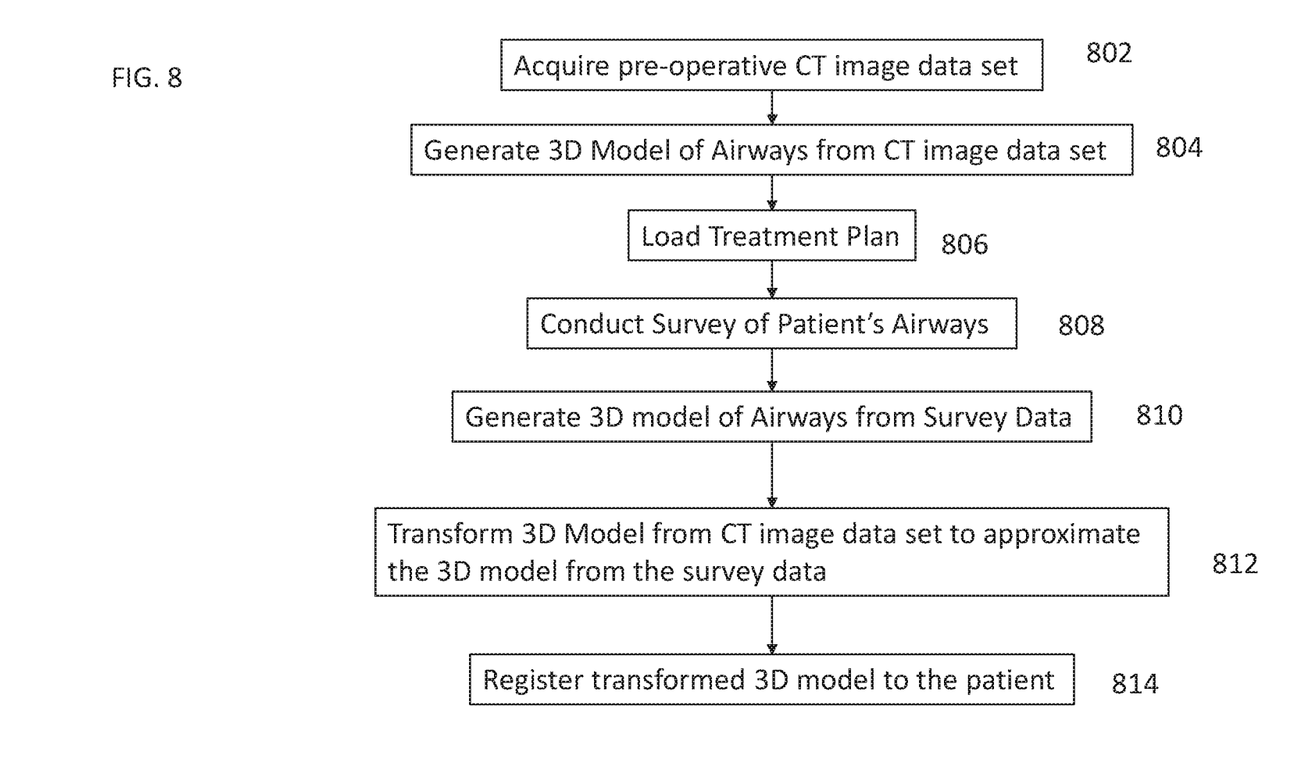
FIG. 8 is a flowchart showing an exemplary method of transforming a pre-procedural CT image data set to correspond to survey data.

A further aspect of the disclosure is described with reference to FIG. 8. In FIG. 8 a method is described to improve the relationship between a 3D model and sensor data received from a position sensor (e.g., EM sensor 94, 95). In accordance with the method, a pre-operative CT image data set is acquired of the patient at step 802. Typically, the pre-operative CT image data set, if of the lungs, is acquired while the patient is at full breath hold. Those of ordinary skill in the art will recognize that other forms of imaging may be employed including CBCT, MRI, fluoroscopy and others without departing from the scope of the disclosure, the one requirement is that the imaging technology be capable of providing images from which a 3D model can be generated. At step 804 a 3D model of the airways is generated from the pre-operative CT image data set. By acquiring the CT image data set at full breath hold, determination of the boundaries of the airways in the 3D model is made easier because the tissue in the image can be more readily distinguished from the airways. Prior to generating the 3D model a treatment plan and the identification of targets within the CT image data set to which a catheter is to be navigated within the patient can be identified and pathways to these targets are established as part of the treatment plan described in greater detail above.

Once the 3D model is generated, the 3D model and treatment plan may be loaded at step 806, into computing device 80 for use by application 81 in conjunction with EMN system 100. After loading of the 3D model and the treatment plan, a survey of the patient's physiology can be undertaken at step 808. In the case of a lung survey, a catheter 96 including a sensor 94, 95 can be inserted into the airways and driven to collect data regarding the shape of the airways in each of the lobes of the lungs. In the case of an EM sensor 94 or 95 being used, as the catheter 96 and sensor is navigated through the airways and into each lobe of the lungs, EM data points are collected. These may be collected at a high frequency (e.g., 100-500 data points per second). The result is a point cloud which resembles the shape of the airways in the lungs. It is understood that in general all of these datapoints will be acquired from within the airways of the lungs.

The data acquired from the survey of the lung by the sensor 94 can be used by the application 81 to generate a 3D model of the airways of the patient at step 810. This 3D model of the airways of the patient may be quite different from the 3D model generated from the pre-operative CT image data. As an initial matter and as noted above the CT image data is typically acquired while the patient is at full breath hold (i.e. maximum inflation) of the lungs, whereas the patient is experiencing tidal volume breathing while the catheter 96 is navigated through the airways to conduct the survey.

Typically, the point cloud generated from the survey will be used by the application 81 to register the 3D model generated from the pre-operative CT image data to the physiology of the patient. In this way, the catheter 96 can be navigated through the airways of the patient without the need of a catheter-based imaging system, but rather by following the pathway and treatment plan through the 3D model generated from the pre-operative CT image data. However, this registration is necessarily inexact owing to the differences in position of the patient's lungs during the capture of the CT image data and during the navigation procedure.

The differences in position of the lungs has been repeatedly observed, and in particular when intra-procedure CBCT images are acquired. Using these intra-procedure CBCT images a plurality of data transforms have been developed. These transforms are developed based on a comparison of the position of certain aspects of the 3D model from the pre-operative CT image data with the position of those same aspects in a 3D model derived from the CBCT images. These aspects may be the locations of bifurcations or other observable aspects of the image data sets. As will be appreciated, the central airways are less likely to move a great deal between the two image data sets, however, the closer one comes to the periphery of the lungs, the greater the opportunity for movement. Thus, the transforms may include a graduation from central to peripheral in the lungs. These transforms are based on hundreds or thousands of comparisons of pre-operative CT image data sets and intra-procedure CBCT images and other data about the patients. Other data may include items such as height, weight, sex, age, prior smoking activities, disease state, body fat, chest diameter, lung capacity, breathing rate, and other data about the patient. From this data numerous transforms can be developed to accommodate most potential patients. These transforms may be stored in the computing device 80 and accessed by the application 81.

At step 312 the application applies one or more of the transforms to the 3D model generated from the pre-operative CT image data and compares the results to the 3D model generated from the point cloud from the survey data collected from the airways of the patient. The transform that results in the closest match to the 3D model generated from the point cloud is utilized to transform the 3D model from the pre-operative CT image data set. This closest match is an approximation of the change in the 3D model generated from the pre-procedure CT image data set to achieve a shape of the airways defined in the 3D model from survey data (e.g., the point cloud).

In some instances, scaling may be necessary for application of the transform to a particular transform. This may be necessary to compensate for differences in scale (e.g., position of the images in a frame, or distance from the imaging device) from the acquisition of the CT image data set as compared to the scale of the images used to develop the transform. The scaling allows the transforms to be used on a wide array of CT image data sets At step 314, the transformed 3D model is registered to the patient using the point cloud data collected and navigation of the patient's airways to an identified target can commence. This navigation of the patient's airways is now undertaken with heightened confidence in the relative position of the 3D model and the actual locations of the catheter 96 within the airways of the patient. Effectively, the application of the transform eliminates much of the CT-to-body divergence that is experienced based on differences in timing, positing, and breathing attributes, etc. between when the CT image data is collected and when the survey or point cloud data is collected.

As described above with respect to FIG. 7, the transform need not be applied globally to the entirety of the pre-procedure CT image data set, but rather can be selectively applied to portions of the CT image data set so that a best fit of the transforms can be applied to select portions. In this way each lobe of the lung, or a separation of left and right lungs, or another division may be employed and a different transform applied to each of these sub-units of the lungs to achieve an ever closer transform of the pre-procedure CT image data set and the 3D model derived therefrom to the 3D model generated from the survey data (e.g., the point cloud) of the airways of the patient.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of registering a luminal network to a 3D model of the luminal network, the method comprising:
    generating a three-dimensional (3D) model from a plurality of images of a luminal network;
    receiving location data associated with a location sensor on a tool navigating the luminal network;
    identifying a plurality of potential matches in the 3D model with the location data;
    applying a deformation model to at least a portion of the 3D model;
    assigning registration scores to the potential matches in the 3D model with the location data based on the deformation model; and
    displaying one of the plurality of potential matches having a highest registration score.

2. The method of claim 1, wherein the assigning of the registration score is further based on at least one of:
    a distance between the potential match and the location data; or
    a difference in direction between location sensor direction data and a direction of the potential match.

3. The method of claim 1, further comprising:
    receiving further location data; and
    reassigning the one of the plurality of potential matches an updated registration score based on the further location data.

4. The method of claim 1, wherein anchor points in the luminal network are used to constrain the registration.

5. The method of claim 1, further comprising discarding any of the plurality of potential matches assigned a low registration score.

6. The method of claim 5, further comprising delaying discarding potential matches with low registration scores when the potential matches are in a bifurcation area of the 3D model.

7. The method of claim 1, further comprising:
    identifying a first region of the luminal network and a second region of the luminal network, wherein the deformation model includes at least one of:
        modeling at least one of rotation, compression, extension, or bending for the first region and the second region independently;
        modeling at least one of rotation, compression, extension, or bending for the first region and the second region with adjacent regions having interdependence; or performing rigid registration of the first and second regions to form first and second rigid registrations, and stitching together the first and second rigid registrations.

8. The method of claim 1, wherein:
the luminal network is a bronchial airway; and
the deformation model comprises applying a moving window from a trachea to a periphery of the bronchial airway, and performing a rigid registration in the moving window.

9. The method of claim 1, wherein the deformation model comprises at least one of:
weighing registration for central areas of the luminal network greater than peripheral areas of the luminal network;
using deformation models having different deformation characteristics for at least two of a right lung, a left lung, or each lung lobe of the luminal network;
using a biomechanical model of the luminal network based on finite image analysis;
using a deformation model based on a specific disease; or
using at least one of a bronchoscope model and a catheter model to produce a specific deformation model.

10. A system for registering a luminal network to a 3D model of the luminal network, the system comprising:
a location sensor on a tool configured to be navigated within a luminal network;
a tracking system configured to detect a location of the location sensor within luminal network; and
a computing device including a processor and a memory storing instructions which, when executed by the processor, cause the computing device to:
generate a three-dimensional (3D) model from a plurality of images of a luminal network;
receive location data associated with the location sensor on the tool navigating the luminal network;
identify a plurality of potential matches in the 3D model with the location data;
apply a deformation model to at least a portion of the 3D model;
assign registration scores to the potential matches in the 3D model with the location data based on the deformation model; and
display one of the plurality of potential matches having a highest registration score.

11. The system of claim 10, wherein the assigning of the registration score is further based on at least one of:
a distance between the potential match and the location data; or
a difference in direction between location sensor direction data and a direction of the potential match.

12. The system of claim 10, further comprising instructions which when executed by the processor, cause the computing device to:
receive further location data and reassign at least one of the potential matches an updated registration score based on the further location data.

13. The system of claim 10, wherein the instructions when executed by the processor, cause the computing device to:
identify a first region of the luminal network and a second region of the luminal network, wherein the deformation model executes steps of at least one of:
model at least one of rotation, compression, extension, or bending for the first region and the second region independently;
model at least one of rotation, compression, extension, or bending for the first region and the second region with adjacent regions having interdependence; or
perform rigid registration of the first and second regions to form first and second rigid registrations, and stitching together the first and second rigid registrations.

14. The system of claim 10, wherein the luminal network is a patient's lung airways, wherein the deformation model weighs registration for central areas of the lungs greater than peripheral areas of the lungs.

15. The system of claim 10, wherein the instructions when executed by the processor, cause the computing device to:
employ a deformation model having different deformation characteristics for one or more of a right lung, a left lung, or each lung lobe.

16. The system of claim 10, wherein the deformation model is one or more of:
a biomechanical model of a patient's lungs based on finite image analysis;
a deformation model based on a specific disease; or
a catheter navigation based model.

17. A system for registering a luminal network to a 3D model of the luminal network, the system comprising:
a location sensor on a tool configured to be navigated within a luminal network;
a tracking system configured to detect a location of the location sensor within luminal network; and
a computing device including a processor and a memory storing instructions which, when executed by the processor, cause the computing device to:
generate a three-dimensional (3D) model from a plurality of images of a luminal network;
receive location data associated with the location sensor on the tool navigating the luminal network;
identify a plurality of potential matches in the 3D model with the location data;
apply a deformation model to at least a portion of the 3D model;
assign registration scores to the potential matches in the 3D model with the location data based on the deformation model, wherein the assigning of the registration score is further based on at least one of:
a distance between the potential match and the location data; or
a difference in direction between location sensor direction data and a direction of the potential match; and
display one of the plurality of potential matches having a highest registration score.

18. The system of claim 17, wherein the instructions when executed by the processor, cause the computing device to:
identify a first region of the luminal network and a second region of the luminal network, wherein the deformation model executes steps of at least one of:
model at least one of rotation, compression, extension, or bending for the first region and the second region independently;
model at least one of rotation, compression, extension, or bending for the first region and the second region with adjacent regions having interdependence; or
perform rigid registration of the first and second regions to form first and second rigid registrations, and stitching together the first and second rigid registrations.

19. The system of claim 17, wherein the luminal network is the airways of a patient's lungs, wherein the deformation model weighs registration for central areas of the lungs greater than peripheral areas of the lungs.

20. The system of claim 17, wherein the instructions when executed by the processor, cause the computing device to:
   employ a deformation model having different deformation characteristics for one or more of a right lung, a left lung, or each lung lobe.

* * * * *